United States Patent [19]

Hibbard

[11] Patent Number: 5,704,932
[45] Date of Patent: Jan. 6, 1998

[54] SANITARY NAPKIN

[76] Inventor: Karen J. Hibbard, RR 1 Box 98, Ferrisburgh, Vt. 05456

[21] Appl. No.: 534,482

[22] Filed: Sep. 27, 1995

[51] Int. Cl.⁶ .................................................. A61F 13/15
[52] U.S. Cl. ...................... 604/387; 604/385.1; 604/386
[58] Field of Search .................... 604/385.1–402

[56] References Cited

FOREIGN PATENT DOCUMENTS

| 60-178230 | 11/1985 | Japan | 604/387 |
|---|---|---|---|
| 5177 | 1/1993 | Japan | 604/387 |
| 549660 | 3/1993 | Japan | 604/387 |
| 6121812 | 5/1994 | Japan | 604/396 |

*Primary Examiner*—John G. Weiss
*Assistant Examiner*—K. M. Reichle

[57] ABSTRACT

A sanitary napkin including a plurality of absorbent pad components detachably adhered one to another to form a singular sanitary napkin. Each absorbent pad component formed as a first outer layer, a second centrally disposable layer, and a third layer. Included is a first adhesive strip adapted to detachably adhere a single bottommost of the absorbent pad components to a crotch portion of a feminine undergarment. Also included are additional adhesive strips which affix supplementary absorbent pad components upon the single bottommost of the absorbent pad components. The plurality of absorbent pad components is numerically greater than two. Lastly, an excess of absorbent filler material is included. The excess of absorbent filler material is to enthicken the single bottommost of the absorbent pad components and is capable of enhancing absorption capabilities.

1 Claim, 3 Drawing Sheets

SANITARY NAPKIN

BACKGROUND OF THE INVENTION

1. Field of the Invention

The present invention relates to a sanitary napkin and more particularly pertains to sanitary napkins which may be employed thereby providing a multi-layered sanitary napkin providing multiple uses in a single napkin appliance and further having a bottommost layer thicker than the other multiple layer components of the sanitary napkins.

2. Description of the Prior Art

The use of absorbent sanitary napkins is known in the prior art. More specifically, absorbent sanitary napkins heretofore devised and utilized for the purpose of absorbing menstrual flow are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 5,169,394 to Jean discloses a feminine sanitary napkin. U.S. Pat. No. 5,135,521 to Luceri and Parr discloses a sanitary napkin with composite cover 300. As shown in FIG. 2, the cover of Luceri includes an outer layer 302 containing fluid passageways which are small enough so that liquid will not flow therethrough. Also, as indicated by the figure, adhesive strips 308 are situated on a bottom face thereof. U.S. Pat. No. 5,037,417 to Ternstrom discloses a sanitary napkin. U.S. Pat. No. 5,004,465 to Ternstrom and Erikson discloses a disposable absorbent article with multiple layers. Lastly, U.S. Pat. No. 4,636,209 to Lassen discloses a sanitary napkin with fluid transfer layer. As shown in FIG. 1, the napkin of Lassen 200 includes a plurality of stacked layers of absorbent material all encapsulated within a permeable cover. The Lassen napkin further includes an impermeable baffle 208 also situated within the composite cover for encompassing only the lower and peripheral portions of the stacked layers of absorbent material 204.

While these devices fulfill their respective, particular objectives and requirements, the aforementioned patents do not describe a sanitary napkin that provides a sanitary napkin which may be employed thereby providing a multi-layered sanitary napkin providing multiple uses in a single napkin appliance and further having a bottommost layer thicker than the other multiple layers components of the sanitary napkins.

In this respect, the sanitary napkin according to the present invention substantially departs from the conventional concepts and designs of the prior art, and in doing so provides an apparatus primarily developed for the purpose of providing sanitary napkins which may be employed thereby providing a multi-layered sanitary napkin providing multiple uses in a single napkin appliance and further having a bottommost layer thicker than the other multiple layer components of the sanitary napkins.

Therefore, it can be appreciated that there exists a continuing need for a new and improved sanitary napkin which can be used as a sanitary napkin which may be employed thereby providing a multi-layered sanitary napkin providing multiple uses in a single napkin appliance and further having a bottommost layer thicker than the other multiple layers components of the sanitary napkins. In this regard, the present invention substantially fulfills this need.

SUMMARY OF THE INVENTION

In view of the foregoing disadvantages inherent in the known types of absorbent sanitary napkins now present in the prior art, the present invention provides an improved sanitary napkin. As such, the general purpose of the present invention, which will be described subsequently in greater detail, is to provide a new and improved absorbent sanitary napkin and method which has all the advantages of the prior art and none of the disadvantages.

To attain this, the present invention essentially comprises a plurality of substantially elongated absorbent pad components. The elongated absorbent pad components are detachably adhered one to another and thereby form a singular sanitary napkin. Each absorbent pad component is formed of a first fluid permeable outer layer, a second centrally disposed absorbent filler layer, and a third fluid impermeable layer. The fluid permeable outer layer is formed of a polymeric film for permitting fluid transfer to the absorbent filler layer. The polymeric film is porous and hydrophobic. The third fluid impermeable layer is formed of a polymeric film. Each absorbent pad has an equal length of about eight to ten inches. The second centrally disposed absorbent filler layer is bonded to the surface of a third layer. The second absorbent filler layer is composed of a thin layer of highly absorbent low density material that is formed from a combination of cellulose and cotton. Also included is a first adhesive strip. The first adhesive strip is adapted to detachably adhere a single bottommost of the fluid absorbent pad components to a crotch portion of a feminine undergarment. The first adhesive strip is linearly positioned along the third layer of the bottommost pad component and is covers about twenty-five percent of the bottommost surface thereof. A cover strip is included. The cover strip overlays the adhesive strip of the single bottommost pad component and is released prior to placement of the single bottommost pad on the crotch portion of the feminine undergarment. Furthermore, additional adhesive strips are included. These additional adhesive strips detachably affix supplementary absorbent pad components upon the single bottommost pad component of the absorbent pad components. The additional adhesive strips are ten percent of a bottom portion of the third layer of another of the absorbent pad components. The plurality of substantially elongated absorbent pad components is numerically greater than two. Lastly, an excess of absorbent filler material is included. The excess of absorbent filler material is to enthicken the single bottommost pad component of the absorbent pad components. The excess filler material contained within the single bottommost pad is about fifty percent greater than the absorbent filler material of another of the absorbent pad components. The excess absorbent filler material is capable of enhancing absorption capabilities of the single bottommost pad component of the absorbent pad components. Finally, the single enthickened pad member is detachably affixed to the crotch portion of a feminine undergarment.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sanitary napkin which has all of the advantages of the prior art absorbent sanitary napkins and none of the disadvantages.

It is another object of the present invention to provide a new and improved sanitary napkin which may be easily and efficiently manufactured and marketed.

It is further object of the present invention to provide a new and improved sanitary napkin which is of durable and reliable constructions.

An even further object of the present invention is to provide a new and improved sanitary napkin which is susceptible of a low cost of manufacture with regard to both materials and labor, and which accordingly is then susceptible of low prices of sale to the consuming public, thereby making such sanitary napkin economically available to the buying public.

Still yet another object of the present invention is to provide a new and improved sanitary napkin which provides in the apparatuses and methods of the prior art some of the advantages thereof, while simultaneously overcoming some of the disadvantages normally associated therewith.

Even still another object of the present invention is to provide a new and improved sanitary napkin having a series of compressed absorbent pad members which are sealedly separated from each and are enable for absorption of menses by manual removal of a protection barrier.

Lastly, it is an object of the present invention to provide a new and improved sanitary napkin including a plurality of substantially elongated absorbent pad components. Each elongated absorbent pad component is detachably adhered one to another to form a singular sanitary napkin. Each absorbent pad component formed with a first outer layer, a second essentially disposed layer, and a third layer. Included is a first adhesive strip adapted to detachably adhere a single bottommost of the absorbent pad components to a crotch portion of a feminine undergarment. Additional adhesive strips are included. The additional adhesive strips are detachably affixing another of the absorbent pad components upon the single bottommost of the absorbent pad components, and additional absorbent pads to another and the single bottommost. The plurality of substantially elongated absorbent pad components is numerically greater than two. Lastly, an excess of absorbent filler material is included. The excess absorbent filler material is to enthicken the single bottommost of the absorbent pad components and is capable of enhancing absorption.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
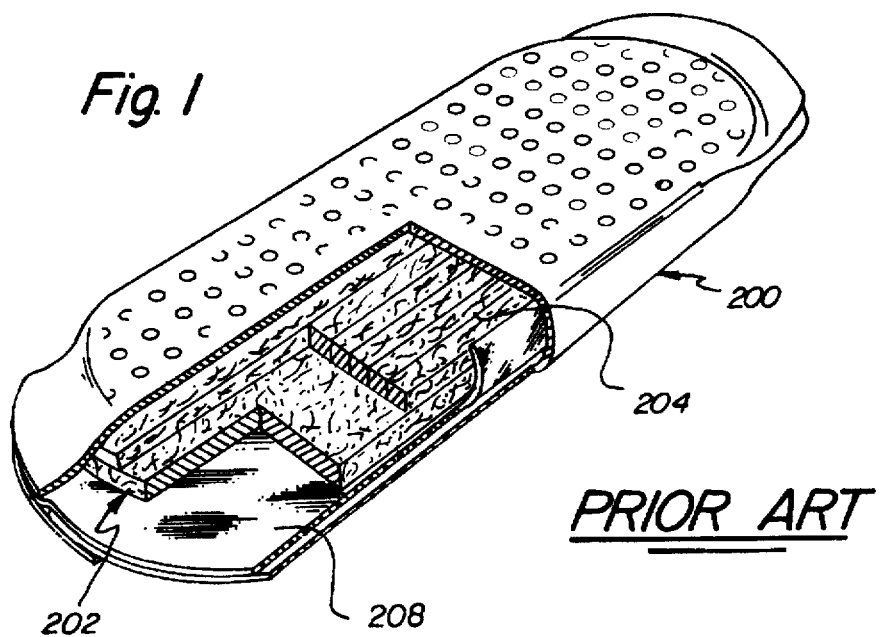
FIG. 1 is a sectional perspective view of the Lassen prior art showing a cut-away of the sanitary napkin thereof.
Figure 2:
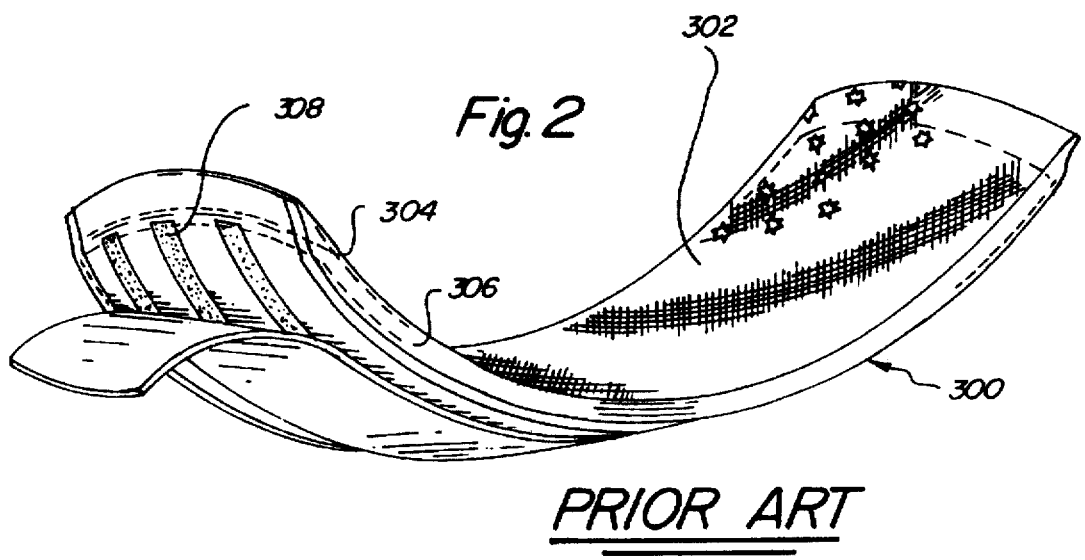
FIG. 2 is a perspective of the Lucri prior art showing the disposition of an adhesive strip applied thereon.
Figure 3:
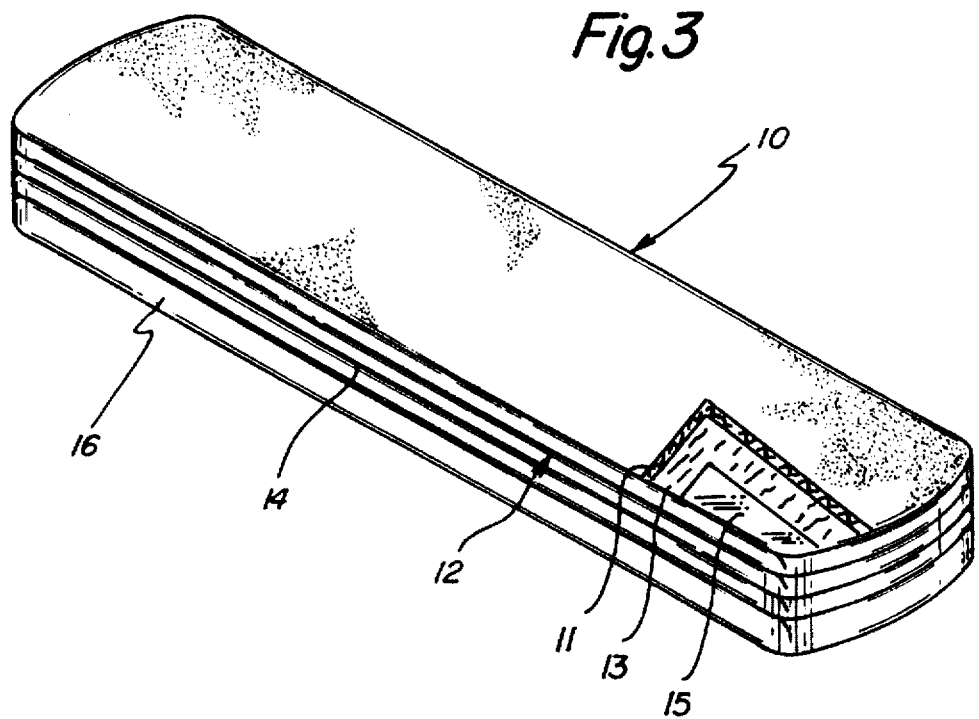
FIG. 3 is a top perspective view of the sanitary napkin showing the layered construction, wherein the napkin is partially sectioned.

With reference now to the drawings, and in particular to FIG. 3 thereof, the preferred embodiment of the new and improved sanitary napkin embodying the principles and concepts of the present invention and generally designated by the reference numeral 10 will be described.

The present invention, the sanitary napkin 10 is comprised of a plurality of components. Such components in their broadest context include thin elongated absorbent pad members, an adhesive strip, a bottommost absorbent pad component. Such components are individually configured and correlated with respect to each other so as to attain the desired objective.

Specifically, the present invention includes a plurality of substantially elongated absorbent pad components 12. Each elongated absorbent pad component detachably adheres one to another to form a singular sanitary napkin. Each absorbent pad component is formed of a first fluid permeable outer layer 11, a second centrally disposed absorbent filler layer 13, and a third fluid impermeable layer 15. The first fluid outer layer is formed of a polymeric film that permits fluid transfer to the absorbent filler layer. The polymeric film is porous and hydrophobic. This allows the material to remain dry when positioned next to the body. The third fluid impermeable layer is made of a polymeric film that is impervious to moisture. Each absorbent pad has an equal length of about eight to ten inches. This uniformity in length and width allows for comfort of the pad when worn by the female.

The second essentially disposed absorbent filler layer 13 is bonded to the surface of the third layer. The second absorbent filler layer is composed of a thin layer of highly absorbent low density material formed from a combination of cellulose and cotton. This material attracts the menses that passes through the first layer 11, which is hydrophobic to absorb the menses.

Figure 4:
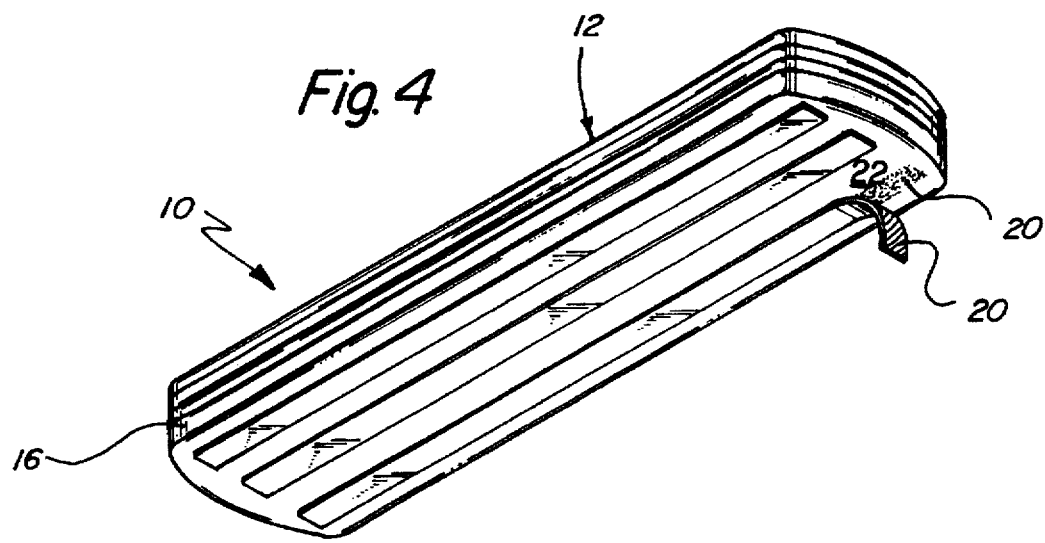
FIG. 4 is a bottom perspective view of the sanitary napkin showing an adhesive strip attachment.

Also included, as shown in FIG. 4 is a first adhesive strip 20. The first adhesive strip is adapted to detachably adhere a single bottommost 16 of the fluid absorbent pad components to a crotch portion of a feminine undergarment. The first adhesive strip is linearly positioned along the third layer of the bottommost pad component and covers about twenty-five percent of a bottom surface 22 thereof. A cover strip 24, as shown in FIG. 4, is positioned over the adhesive strip of the single bottommost pad component and is released prior to placement of the singe bottommost pad.

Figure 6:
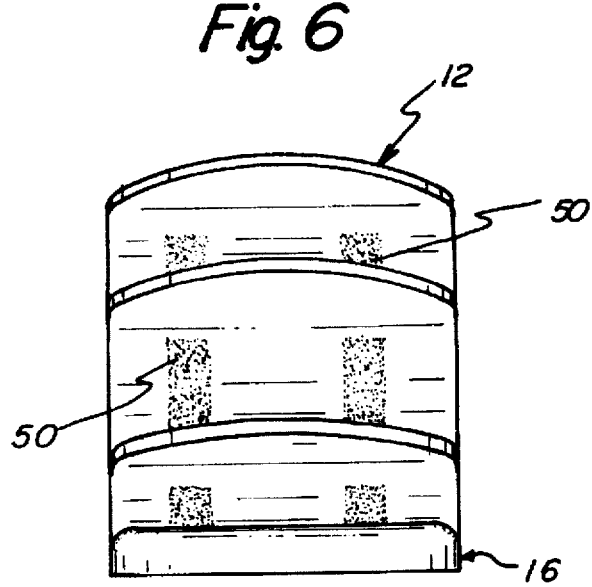
FIG. 6 is a side sectional view of a partially exploded sanitary napkin of the present invention taken substantially along the plane indicated by the section line 6—6 of FIG. 5.

As best illustrated in FIG. 6, additional adhesive strips are included. These additional adhesive strips 50 detachably affix supplementary absorbent pad components 12 upon the single bottommost of the absorbent pad components. The additionally adhesive strips are ten percent of a bottom portion of the third layer of another of the absorbent pad components.

Figure 5:
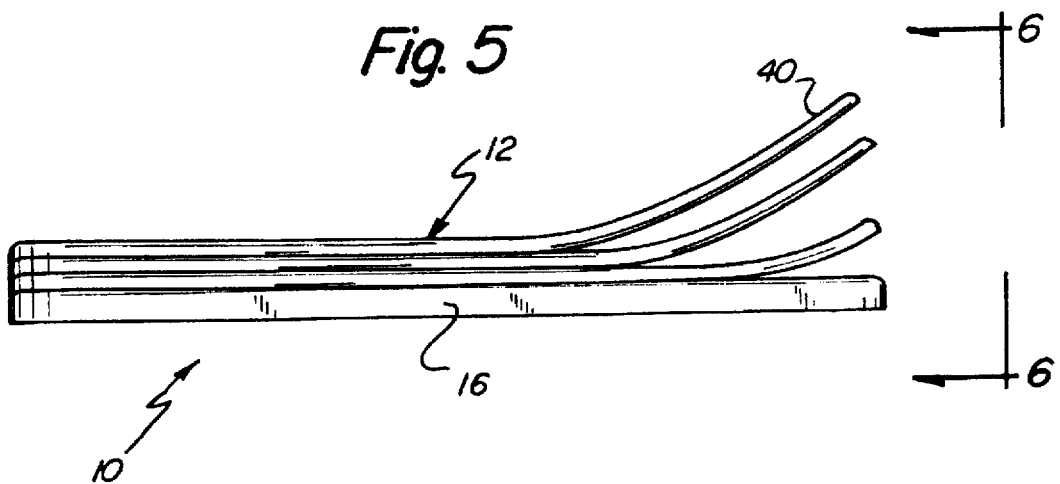
FIG. 5 is a partially exploded side elevational view of the sanitary napkin showing the separation of layers.

The plurality of substantially elongated absorbent pad components, as shown in FIG. 5 is numerically greater than two. As shown in the present invention, preferably there are four absorbent pads with the bottommost pad being the fourth and most absorbent. Additionally, as shown in FIG. 5 the thin elongated absorbent pad members 12 detachably affix upon each other at interfaces 14, as shown in FIG. 3. Furthermore, the thin elongated absorbent pad components have convex curved sides designed to better fit the female human form.

Lastly, an excess of absorbent filler material is included. The excess of absorbent filler material 13 is to enthicken the single bottommost 16 of the absorbent pad components. The excess of absorbent filler material contained within the single bottommost pad is about fifty percent greater than the absorbent filler material of another of the absorbent pad components. The excess of absorbent filler material is capable of enhancing absorption. The single enthicken pad member is detachably affixed to the crotch portion of a feminine undergarment.

In FIG. 5, of the four impermeable barriers, the third layer 40 is shown being separated from the remaining layers. This layer has a membranous film 15 which precludes the menses from accessing any of the adjacently disposed pad components 12 or 16. The pad components are joined by detachably adhesive strips 50 to provide for removal of individual pad components whenever a pad component is considered expended. Wherein, the expended pad member is stripably removed from the adjacent pad component 12 or 16 and discarded. Removal of the expended pad component 12 exposes an absorbent surface of an underlying unused pad component which remains attached to the undergarment or panty, thereby providing for continued and multiple use of the sanitary napkin 10.

The present invention is a sanitary napkin that has four layers with the bottom layer being an enthicken layer. Each of the four layers are equal in length, with the upper layer being thin elongated absorbent pad components. The sanitary napkin is a peel-away sanitary napkin that has multiple layers. The layers are attached one to another with a light adhesive strip that is non-irritant material. The sanitary napkin of the present invention improves comfort of women who are menstruating.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sanitary napkin with individually disposable absorbent pad components comprising in combination:

at least three substantially elongated absorbent pad components detachably adhered to each other thereby forming a singular sanitary napkin, each absorbent pad component formed of a first, fluid permeable outer layer, a second, centrally disposed, absorbent filler layer, and a third, fluid impermeable layer, each first, fluid permeable outer layer being formed of a polymeric film permitting fluid transfer to the absorbent filler layer, the polymeric film being porous and hydrophobic, each third, fluid impermeable layer comprising a polymeric film, each absorbent pad component having an equal length of about 8 to 10 inches;

each second, centrally disposed, absorbent filler layer being bonded to a top surface of the third layer and the first layer joined to the second and third layers, each second, absorbent filler layer being composed of a thin layer of highly absorbent, low density material formed from a combination of cellulose and cotton;

a first adhesive strip adapted to detachably adhere one of said at least three pad components to a crotch portion of a feminine undergarment, the first adhesive strip linearly positioned along the third layer of said one pad component and covering about 25 percent of a bottom surface thereof, a cover strip overlaying the adhesive strip of said one pad component and being releasable prior to placement of said one pad component;

additional adhesive strips detachably affixing the remainer of said at least three absorbent pad components stacked upon said one pad component, the additional adhesive strips covering 10 percent of a bottom portion of the third layer of each of the remaining absorbent pad components; and said one pad component including an additional amount of highly absorbent, low density material in its second layer, the additional amount of material contained within said one pad component pad being about fifty percent greater than an amount of absorbent material of the respective second layers of one of the remaining absorbent pad components, the additional amount of material being capable of enhancing absorption capabilities.

* * * * *